(12) United States Patent
Park et al.

(10) Patent No.: US 6,362,320 B1
(45) Date of Patent: Mar. 26, 2002

(54) PROCESS FOR PURIFYING HEPATITIS B VIRAL SURFACE ANTIGEN COMPRISING PRES2 PEPTIDE

(75) Inventors: Soon-Jae Park; Young-Mee Lee; Kyung-Hee Yoon; Kook-Jin Lim; Young-Sun Kwon, all of Daejeon (KR)

(73) Assignee: LG Chemical Limited (KR)

( * ) Notice: Subject to any disclaimer, the term of this patent is extended or adjusted under 35 U.S.C. 154(b) by 0 days.

(21) Appl. No.: 09/432,300

(22) Filed: Nov. 2, 1999

Related U.S. Application Data

(63) Continuation-in-part of application No. 08/991,035, filed on Sep. 29, 1997, now abandoned, which is a continuation-in-part of application No. 08/569,815, filed on Dec. 8, 1995, now abandoned.

(30) Foreign Application Priority Data

Dec. 10, 1994 (KR) ............................................. 94-33594

(51) Int. Cl.$^7$ ................................................. C12N 7/02
(52) U.S. Cl. ........................ 530/412; 530/417; 530/418

(58) Field of Search .......................... 424/227.1, 189.1; 530/412, 417, 418

(56) References Cited

U.S. PATENT DOCUMENTS

| | | | | |
|---|---|---|---|---|
| 4,649,192 A | * | 3/1987 | Van Wijnendaele et al. | |
| 5,340,926 A | * | 8/1994 | Lowe et al. | |

FOREIGN PATENT DOCUMENTS

| | | | |
|---|---|---|---|
| EP | 0 337 492 | * | 10/1989 |
| EP | 0 384 058 | * | 8/1990 |

* cited by examiner

*Primary Examiner*—Anthony C. Caputa
*Assistant Examiner*—Brenda G. Brumback
(74) *Attorney, Agent, or Firm*—Anderson Kill & Olick, PC

(57) ABSTRACT

A process for purifying hepatitis B viral surface antigen comprising the preS2 peptide from the cells of a recombinant organism is carried out by a sequence of steps which includes the step of disrupting the cells using a buffer containing a chaotropic salt to obtain a cell homogenate and the step of alkalifying the cell homogenate to a pH ranging from 11.0 to 13.5.

13 Claims, 1 Drawing Sheet

PROCESS FOR PURIFYING HEPATITIS B VIRAL SURFACE ANTIGEN COMPRISING PRES2 PEPTIDE

CROSS REFERENCES TO RELATED APPLICATION

This application is a continuation-in-part application of U.S. Ser. No. 08/991,035, now abandoned, filed on Sep. 29, 1997, which was a continuation-in-part application of U.S. Ser. No. 08/569,815 filed on Dec. 8, 1995, now abandoned.

FIELD OF THE INVENTION

The present invention relates to a process for purifying hepatitis B viral surface antigen containing a preS2 peptide; and, more specifically, to a process for purifying hepatitis B viral surface antigen containing a preS2 peptide from a recombinant yeast cell, which includes a cell disruption step carried out in the presence of a chaotropic salt to obtain a cell homogenate and the step of alkalifying the cell homogenate to enhance the solubilization of the surface antigen.

BACKGROUND OF THE INVENTION

Hepatitis B is one of the worldwide public health problems and approximately 200 to 300 millions of the world population are said to carry hepatitis B virus("HBV"). The HBV infection frequently progresses into cirrhosis and hepatocellular carcinoma, leading to the possible death of the patient.

Hitherto, no treating agent for hepatitis B has been developed, and, as such, the importance of vaccines has been emphasized.

Blumberg et al. discovered the so-called Australian antigen from the blood of hepatitis B patients in 1955; and Krugman et al. reported, in 1971, an active immunization method using a heat-treated human serum containing HBV, thereby offering the possibility of developing hepatitis B vaccines. Thereafter, the first generation hepatitis B vaccines, which are prepared by separating and purifying a hepatitis B viral surface antigen(HBsAg) from the blood plasma of hepatitis B patients, have been commercialized (M. R. Hilleman et al., *Develop. Bio. Standard*, 54, 3–12 (1983)).

However, the vaccines derived from the blood plasma have the problems that: their purification and inactivation processes are cumbersome and require high costs; supply of human blood is limited; and an inoculated person may be infected with the pathogens from the blood source.

Accordingly, in order to solve the above problems, genetic engineering approaches have been tried in developing hepatitis B vaccines.

For instance, Valenzuela et al. have developed a process for producing HBsAg in yeast(*Nature*, 293, 347–350 (1982)). The recombinant HBsAg(r-HBsAg) consists primarily of S protein(P25) having 226 amino acids, and when purified, it forms surface antigen particles which are almost identical to those of HBsAg separated from blood plasma.

K. H. Heermann et al. have reported that the hepatitis B viral envelope protein contains significant amounts of L-protein(preS1+preS2+S: p39) and M-protein(preS2+S: p31), as well as S-protein(*J. Virol.*, Nov., 396–402 (1984)). The preS1 peptide has been known to play an important role with respect to the onslaught of hepatitis B virus on the liver after it infects human. The preS2 peptide, which consists of 55 amino acids, has been found to help the antibody formation against the surface antigen in animal experiments(D. R. Milich et al.,*Proc. Natl. Acad. Sci. U.S.A.*, 82, 8168–8172 (1985)).

Further, it has been known that antibodies formed against the preS2 peptide exhibit defensive activity against viral infection(Y. Ito et al., *Proc. Natl. Acad. Sci. U.S.A.*, 83, 9174–9178(1986)). Therefore, a vaccine containing the preS2 peptide may be useful to a person who cannot form antibodies against a pre-existing surface antigen. The development of such a vaccine is also important for the protection against infection by recently discovered hepatitis B viral variants.

However, since the pres peptide is very sensitive to proteases present in a yeast cell, preparation of a hepatitis B viral surface antigen containing the pres peptide has met with various difficulties. In order to overcome the difficulties, Kobayashi et al. have produced a vaccine which is prepared by genetically modifying the protease-sensitive region between the preS2 and S peptides(*J. Bacteriology*, 8, 1–22(1988)); and U.S. Pat. No. 4,742,158 discloses a process for producing a vaccine containing the pres peptide, wherein the peptide is protected from protease attack by using a protease inhibitor in the cell disruption step. However, the effect of the genetic modification by Kobayashi et al. on the activity of the preS2 peptide has not been fully characterized, and the latter process is not practical because protease inhibitors are too expensive to be used in a mass purification process. Further, the level of preS2 peptide cannot be maintained beyond a certain amount regardless of the amount of protease inhibitors added when the purification time becomes longer as the purification scale or requirement increases.

European Patent No. 0 337 492 A1 provides a process for purifying HBsAg from the culture of Pichia sp. using potassium thiocyanate. Potassium thiocyanate is used for raising the yield of lipophilic proteins, and the entire process is aimed at the purification of the HBsAg containing the S peptide only. When the HBsAg further contains the preS2 peptide consisting of 55 amino acids in front of the S peptide consisting of 226 amino acids, it has immunological properties similar to those of the surface antigen comprising the S peptide only because the antigenicity and immunogenicity of the S peptide moiety are the same. However, the two surface antigens are inevitably different in their physicochemical properties. In particular, the preS2 peptide is sufficiently hydrophilic to be exposed on the surface of the antigen particle, and, accordingly, its purification requires a special procedure.

Therefore, various processes for purifying the hepatitis B viral surface antigen comprising the preS2 peptide have been developed.

European Patent No. 0 130 178 A1 describes a process for purifying HBsAg comprising the preS2 peptide, which is characterized by separating the surface antigen using two liquid phases which are prepared by adding a suitable amount of dextran and glycol to a yeast extract. However, this process has problems in that: the separated surface antigen is not sufficiently pure; it is not suitable for a large scale purification process because dextran and polyethylene glycol are expensive; and it is not economical due to the fact that an additional procedure is required for the removal of a surfactant used.

U.S. Pat. No. 4,742,158 teaches a process for purifying HBsAg containing the preS2 peptide, which comprises: preparing a yeast extract in the presence of various protease inhibitors and purifying the surface antigen therefrom by a series of column chromatographic separation steps using an affinity column prepared by attaching a human serum albumin polymer to a gel matrix as well as a hydrophobic column eluting with a surfactant. However, this process has such difficiencies as: the protease inhibitors used in the process are very expensive; the affinity column is not suitable for mass purification; and a special procedure is required for the removal of a surfactant used in the hydrophobic column chromatography.

M. Kobayashi et al. have also reported a process for purifying HBsAg comprising the preS2 peptide(*J. of Biotechnology*, 8, 1–22(1988). However, this process is not suitable for mass purification as it employs an immunoaffinity column which gives a low yield.

Korean Patent No. 065305 presents a process for purifying HBsAg, which comprises a pH precipitation, and silica and anion exchange column chromatography. This process has the disadvantage that it is difficult to maintain the preS2 peptide content at a suitable level because the preS2 peptide is digested by proteases during the initial stage of the process.

Therefore, there still exists a need for an efficient process for purifying HBsAg containing the preS2 peptide.

SUMMARY OF THE INVENTION

Accordingly, it is a primary object of the present invention to provide a process for purifying hepatitis B viral surface antigen containing a preS2 peptide from a yeast cell in a sufficiently pure state to be directly incorporated into a vaccine.

In accordance with one aspect of the present invention, there is provided a process for purifying hepatitis B viral surface antigen containing the preS2 peptide, which is expressed in recombinant organism cells, characterized in that the recombinant organism cells are disrupted using a buffer containing a chaotropic salt to obtain a cell homogenate, followed by alkalifying the homogenate to a pH ranging from 11.0 to 13.5 in the presence of a surfactant to enhance the solubilization of the surface antigen.

BRIEF DESCRIPTION OF THE DRAWING

The above and other objects and features of the present invention will become apparent from the following description of the invention, when taken in conjunction with the accompanying drawing, in which.

DETAILED DESCRIPTION OF THE INVENTION

Figure 1:
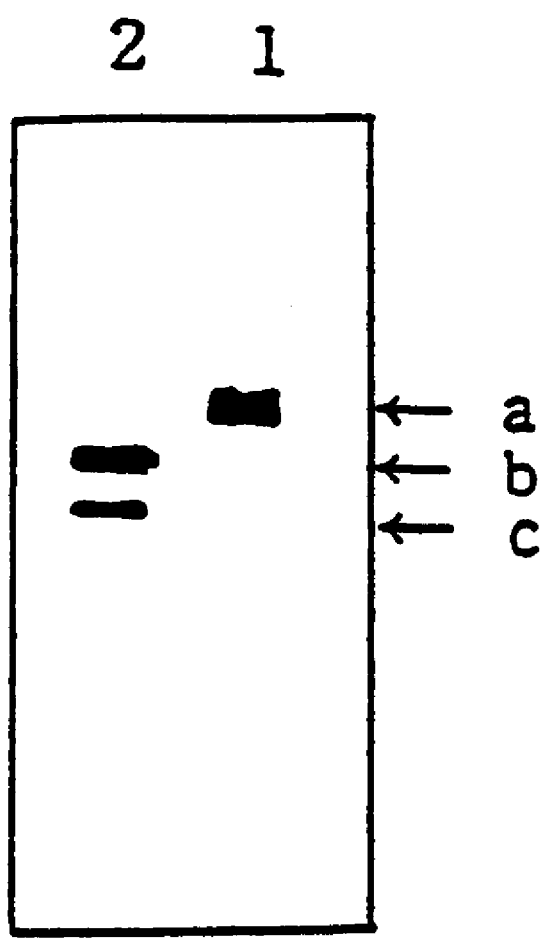
FIG. 1 shows the result of 15% sodium dodecyl sulfate polyacrylamide gel electrophoresis(SDS-PAGE) which verifies the preS2 peptide content in HBsAg when the surface antigen comprising the preS2 peptide is purified in the presence of sodium thiocyanate as the chaotropic salt.

The present invention provides a process for purifying hepatitis B viral surface antigen containing the preS2 peptide expressed in recombinant organism cells, which is characterized in that the recombinant organism cells are disrupted using a buffer containing a chaotropic salt to obtain a cell homogenate and that the cell homogenate thus obtained is alkalified to a pH of 11.0 to 13.5 to enhance the solubilization of the surface antigen. Use of a buffer containing a chaotropic salt in the cell disruption step promotes the formation of HBsAg particles and protects the preS2 peptide from the protease attack which generally takes place during an initial stage of purification, thereby minimizing the loss of the preS2 peptide. More specifically, the process of the present invention may be carried out by the steps of:

(a) disrupting the cells in a buffer containing a chaotropic salt to obtain a cell homogenate;

(b) adding a surfactant to the cell homogenate and alkalifying the homogenate to a pH ranging from 11.0 to 13.5 to enhance the solubilization of the surface antigen;

(c) acidifying the alkalified homogenate obtained in step (b) to a pH ranging from 4.5 to 6.0 to precipitate cell debris, lipids and contaminant proteins;

(d) centrifuging the acidified homogenate obtained in step (c) to obtain a supernatant solution containing the surface antigen;

(e) treating the solution obtained in step (d) with silica to adsorb the surface antigen onto the silica, removing the contaminant proteins by washing and desorbing the surface antigen from the silica using a buffer to obtain a fraction of purified surface antigen;

(f) subjecting the fraction of purified surface antigen obtained in step (e) to hydrophobic column chromatography to obtain fractions containing the surface antigen; and (g) purifying the fractions obtained in step (f) by size exclusive gel filtration chromatography to obtain the surface antigen in a pure form.

The process of the present invention may be applied to a process for purifying HBsAg which is produced in any one of suitable recombinant organism cells, preferably, a recombinant yeast cell, e.g., *Saccharomvces cerevisiae*.

Suitable chaotropic salts which may used in the present invention include sodium thiocyanate, potassium thiocyanate, ammonium thiocyanate, guanidium hydrochloride and urea; whilesodium thiocyanate is preferred.

Any conventional buffer system, e.g., phosphate buffer and Tris buffer, may be used for cell disruption in the process of the present invention; and the pH thereof may preferably be adjusted to a range from 6 to 8. The concentration of the chaotropic salt in the buffer may range from 1 to 8 M, preferably, from 1 to 3 M.

Exemplary surfactants which may be used in step (a) above for extracting the surface antigen from the cell membrane include: TWEEN® 20 (polysorbate 20), TWEEN® 80 (polysorbate 80), TRITOND® X-100 (polyoxyethylene ocylphenylether), and sodium deoxycholate, while TWEEN® 20 is preferred. The surfactant may be used in an amount ranging from 0.1 to 0.5%(w/v), preferably, from 0.1 to 0.2%(w/v), on the basis of the amount of the cell homogenate.

In order to increase the solubility of the surface antigen in the cell homogenate and promote their particle formation, it is preferable to increase the pH of the surface antigen extract to a range from 11.0 to 13.5, by using a base, preferably, sodium hydroxide and potassium hydroxide. This alkalification process is considered to promote the particle formation of HBsAg by increasing the intermolecular disulfide bond and dissociating the contaminant proteins from HBsAg through increased solubility. Thereafter, the extract is preferably allowed to stand at a temperature ranging from 0 to 30° C. for a time period ranging from 0.5 to 1 hour.

Then, the extract is acidified to precipitate the cell debris, lipids and contaminating proteins, wherein the pH of the extract is lowered to a range from 4.5 to 6.0. Representative acids which may be used in this step include any one of inorganic or organic acids, while a 10 to 30% acetic acid solution is preferred. The acidification reaction may be carried out at a temperature ranging from 0 to 30° C. for a time period ranging from 0.5 to 2 hours, preferably with stirring. The acidified extract is centrifuged to remove the resulting precipitates and to obtain a supernatant containing the surface antigen. This procedure is advantageous in that one simple centrifugation step removes the cell debris, lipids and contaminant proteins simultaneously, and that the yield of the surface antigen is high owing to the prior step of dissolving the surface antigen at a high pH.

Heightening and then lowering the pH of the cell extract stabilizes the particle forming property of the surface antigen and is very efficient in removing the lipids and contaminant proteins.

However, when a thiocyanate is used as the chaotropic salt in the cell disruption step, foul smell may be emitted during the acidification step. A thiocyanate salt itself is a color-, odor- and harmless compound and a thiocyanate ion is quite stable in solution. Therefore, the smell generated in the acidification step is considered to originated from reactions of thiocyanate with some substances in the cell extract. This odor may be tolerable to the operator in case of a small-scaled purification, but in a large scale operation, it is preferable to remove said thiocyanate before the acidification step.

For example, thiocyanate may be preferably removed by adding a suitable salt to the cell extract to precipitate thiocyanate salt together with some of the contaminant proteins immediately after, e.g., step (a) above; removing the precipitates by, e.g., centrifugation; and diafiltering the resulting supernatant. The surface antigen does not precipitate during this procedure. Further, the removal of thiocyanate is carried out concomitantly with the removal of a part of the contaminating proteins, which facilitates the subsequent purification processes. Preferred salts which may be used in the deodorization procedure include salts of multiply charged anions, e.g., sodium sulfate and ammonium sulfate, in a concentration ranging from 8 to 15%(w/v). After extracting the surface antigen from the cell membrane, salt is added and the reaction is allowed to proceed at room temperature for 0.5 to 2 hours with or without stirring. The resulting precipitates may be removed by a conventional method, e.g., centrifugation, to obtain a supernatant containing the surface antigen. The resulting supernatant is subjected to repeated diafiltration processes to remove thiocyanate and sulfate. The buffer used in this step preferably has a pH ranging from 6 to 8. When the steps of salt treatment, centrifugation and diafiltration are completed, the resulting supernatant is subjected to step (b) and (c).

The supernatant obtained in step (c), which contains the surface antigen, is treated with silica using a column or batch method, while the batch method is preferred. Suitable silica for this step is a microcrystalline silica having a surface area ranging from 100 to 500 mm$^2$/g; and, preferably, Aerosil® 380 (Degussa, Germany) may be used. The supernatant containing the surface antigen is brought into contact with a silica slurry at a pH ranging from 6 to 8 and a temperature ranging from 4 to 30° C. for a time period ranging from 2 to 16 hours with vigorous stirring. The amount of silica used for the adsorption of the surface antigen is preferably about 5%(w/w) on the basis of the weight of cell cake. The surface antigen-silica complex is separated from the solution by using a conventional method, e.g., centrifugation.

Thereafter, the complex is washed, e.g., three times with a buffer having a pH ranging from 6 to 8, preferably, a sodium phosphate-sodium chloride buffer, to remove the residual contaminant proteins from the silica. The surface antigen may be desorbed from the silica by contacting the complex with a suitable buffer for about 2 hours. A buffer having a pH ranging from 8.8 to 11.0, preferably, a sodium carbonate-sodium bicarbonate buffer, may be suitably used in this step. The buffer may further contain urea in a concentration ranging from 1 to 8 M and a surfactant, preferably, sodium deoxycholate, in a concentration ranging from 0.1 to 0.3 wt. %. Then the silica is removed from the solution by using a conventional method, e.g., centrifugation, to obtain a supernatant containing the surface antigen. However, when sodium deoxycholate is used in the desorption step, it is necessary to remove it via repeated diafiltration.

The supernatant obtained above, which contains the surface antigen, may be further purified by hydrophobic column chromatography, wherein an agarose gel having phenyl residues, a hydrophobic resin, is preferably used. Before the supernatant contacts the hydrophobic resin, the filling material, i.e., the hydrophobic resin, is equilibrated with a buffer having a pH ranging from 8.8 to 11.0, which may be the same buffer as the one used in the prior step. The buffer may preferably contain urea in a concentration ranging from 1 to 4 M to maximally remove the contaminant proteins which are less hydrophobic than the surface antigen.

Then the supernatant containing the surface antigen is passed through the column to contact with the filling material therein. The column is thoroughly washed with the equilibrium buffer containing 10–40 wt. % ethylene glycol to remove the relatively weakly adsorbed contaminant proteins from the filling material. Then the surface antigen bound to the hydrophobic resin is eluted with the equilibrium buffer containing 60 to 80 wt. % ethylene glycol.

This hydrophobic column chromatography represents a very efficient purification step, wherein most of the remaining contaminants in the supernatant after the silica adsorption step can be removed. In particular, pyrogenic materials which are hard to remove by a conventional method can be removed via this step. Urea and ethylene glycol which remain in the fractions containing the surface antigen may be removed, e.g., by dialysis or by repeated diafiltration, wherein a buffer having a pH ranging from 6 to 8 is preferably used.

The fractions containing the surface antigen obtained from the hydrophobic column chromatography are further purified by size exclusive gel filtration chromatography to an extent that the purified antigen can be used in the preparation of a vaccine.

The exemplary polar matrices which may be used as the column filling material include, e.g., agarose gel, dextran gel and polyacrylamide gel, having a molecular weight cut-off value of at least 1,000,000, preferably from 5,000 to 500,000. The size exclusive gel filtration chromatography is carried out by passing the fractions containing the surface antigen through a column equilibrated with Tris or phosphate buffer having a pH ranging from 6 to 8, which contains sodium chloride in a concentration ranging from 0.1 to 0.2 M; and eluting the surface antigen with the same buffer.

The fractions containing the surface antigen are combined together and the purity of the surface antigen and the preS2 peptide contained therein are determined with SDS-PAGE. As verified through various experiments in the following Examples, the surface antigen purified by the process of the present invention is so pure and the content of preS2 peptide thereof is so high that the purified antigen can be directly used in the preparation of a vaccine.

The following Examples and Comparative Example are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE 1

(Step 1) Disruption of Yeast Cell

Recombinant *Saccharomyces cerevisiae* KCTC 0098BP, which is capable of expressing a hepatitis B surface antigen comprising the preS2 peptide, was cultured at 270° C. in 30 l of YEPD medium(1% yeast extract, 2% yeast peptone, 1.6% glucose). 70 g of yeast cell cake, thus obtained, was mixed with 140 ml of a buffer designated buffer 1(50 mM Tris, pH 7.2, 1 M sodium thiocyanate, 0.15M sodium chloride, 10 mM ethylene diamine tetraacetic acid(EDTA), and 1 mM phenyl methyl sulfonyl fluoride (PMSF)), and the mixture was added to the container of a bead beater(Biospec Products, OKLA, U.S.A.) containing 210 ml of glass beads having a diameter of 0.5 mm.

The container was submerged in ice-water and the bead beater was operated three times at 15 min. interval, each for 5 min. The resulting cell homogenate was separated from glass beads, the glass beads were washed with 210 mt of buffer 1, and the wash solution was combined with the cell homogenate.

(Step 2) Extraction and Dissolution of the Surface Antigen

To the cell homogenate obtained in (Step 1), Tween 20 was added to a concentration of 0.1%(w/v) and the mixture was stirred at room temperature for 2 hours.

The solution was adjusted to pH 11.5 by the addition of 5 N sodium hydroxide and stirred at room temperature for 1 hour. The resulting solution was adjusted to pH 5.2 by the addition of 20% acetic acid, stirred at room temperature for 30 min. and then allowed to stand for 30 min.

The solution was centrifuged at 80° C. to remove the cell debris together with the precipitates.

The supernatant containing the surface antigen was adjusted to pH 7.2 by the addition of 5 N sodium hydroxide. At this point, the volume of the supernatant was about 300 ml.

(Step 3) Adsorption and Desorption Using Silica

Dried silica was mixed with water to make a 5% slurry (dry weight/volume of slurry), 70 me thereof was added to the supernatant obtained in (Step 2), and the mixture was stirred at room temperature for 2 hours. The resulting solution was centrifuged at 5,500 rpm for 10 min. to remove the supernatant, and the precipitated silica, whereto the surface antigen was adsorbed, was washed two times with phosphate buffer(pH 7.2) containing 0.15 M sodium chloride.

The washed silica was added to 70 me of 50 mM carbonate buffer(pH 9.5) containing 1 M urea and the mixture was stirred at room temperature for 1 hour to desorb the surface antigen from the silica. At this point, the pH of the buffer was 9.2. The solution was centrifuged(Beckman JA14 rotor) at 12,000 rpm for 30 min. to obtain a supernatant containing the surface antigen.

The amount of the hepatitis B viral surface antigen in the supernatant was about 6.5 mg, as was measured with AUSZYME® kit (Abbott, U.S.A.).

COMPARATIVE EXAMPLE 1

The same procedures as in Example 1 were repeated, except that sodium thiocyanate was not included in the buffer 1, to obtain the purified surface antigen solution. As a result, the amount of the hepatitis B viral surface antigen in the supernatant was about 7.1 mg, when measured with Auszyme kit.

The surface antigen solutions obtained in Example and Comparative Example were subjected to 15% sodium dodecyl sulfate-polyacrylamide gel electrophoresis(SDS-PAGE), followed by silver staining. The result is shown in FIG. 1, wherein lanes 1 and 2 represent the surface antigen solutions obtained in Example 1 and Comparative Example, respectively. Here A indicates an intact protein band; and B and C, the protein fragments resulted from the protease attack.

As shown in FIG. 1, the surface antigen comprising a high preS2 peptide content can be purified from yeast cells in a high yield in accordance with the process of the present invention.

COMPARATIVE EXAMPLE 2

The procedure of Example 1, steps 1 and 2 were repeated except that the step of adding 5N sodium hydroxide to adjust the pH to 11.5(in step 2) was omitted. The antigenicity of the supernatant obtained after the centrifugation was only 63% of that observed in Example 1, while the O.D at 600 nm was observed to be 1.76 which is significantly higher than the O.D. value of 0.07 observed in Example 1. These results show that when the alkalifying step is omitted, the antigenicity become lows and the amount of contaminant proteins increases.

EXAMPLE 2

Recombinant *Saccharomyces cerevisiae* KCTC 0098BP, which is capable of expressing a hepatitis B surface antigen comprising the preS2 peptide, was cultured at 27° C. in 300 l of YEPD medium. 3 kg of yeast cell cake, thus obtained, was mixed with 6 l of buffer 1 and the mixture was passed twice through DYNOMILL® (Glenmills, Japan) containing 3 l of glass beads having a diameter of 0. 5 mm, at 10° C. at a flow rate of 650 ml/min. to disrupt the yeast cells.

The resulting cell homogenate was separated from glass beads, the glass beads were washed with 9 l of buffer 1, and the wash solution was combined with the cell homogenate. The amount of the HbsAG in the supernatant was about 754 mg, when measured with AUSZYME® kit.

(Step 2) Extraction and Dissolution of the Surface Antigen

To the cell homogenate obtained in (Step 1), Tween 20 was added to a concentration of 0.1%(w/v) and the mixture was stirred at room temperature for 2 hours.

The solution was adjusted to pH 11.5 by the addition of 5 N sodium hydroxide and stirred at room temperature for 1 hour. The resulting solution was adjusted to pH 5.2 by the addition of 20% acetic acid, stirred at room temperature for 30 min. and then allowed to stand for 30 min.

The solution was centrifuged at 8° C. to remove the cell debris together with the precipitates.

The supernatant containing the surface antigen was adjusted to pH 7.2 by the addition of 5 N sodium hydroxide. As a result, the volume of the supernatant was finally about 12 l, and the amount of the HBsAg in the supernatant was about 1,250 mg, when measured with Auszyme kit.

The yield of the surface antigen was 165.8% on the basis of the amount of the surface antigen determined in (Step 1). This unexpectedly high yield is mainly due to the combined actions of the surfactant and the alkali, which increase the antigenicity and promote the solubility of the surface antigen.

(Step 3) Adsorption and Desorption Using Silica

The supernatant obtained in (Step 2) was diluted with twofold volume of 0.15 M sodium chloride and then adsorbed onto silica(Aerosil 380) in accordance with the following procedure. Dried silica was mixed with water to make a 10% slurry(dry weight/volume of slurry), 1.5 e thereof was added to the supernatant obtained in (Step 2), and the mixture was stirred at 4° C. overnight.

The resulting solution was centrifuged at 5,500 rpm for 10 min. to remove the supernatant, and the precipitated silica, whereto the surface antigen was adsorbed, was washed twice with phosphate buffer(pH 7.2) containing 0.15 M sodium chloride.

The washed silica was added to 3 E of 50 mM carbonate buffer(pH 9.5) containing 1 M urea and the mixture was stirred at room temperature for 2 hours to desorb the surface antigen from the silica. At this point, the buffer showed pH 9.2. The solution was centrifuged at 8,700 rpm for 30 min. to obtain a supernatant containing the surface antigen.

The amount of the HbsAG in the supernatant was about 895 mg, when measured with AUSZYME® kit (yield: 118.7%).

(Step 4) Hydrophobic Column Chromatography

To the supernatant obtained in (Step 3) containing the surface antigen was added urea to a final concentration of 4 M, and the resulting solution was passed through a phenyl agarose column which was equilibrated with 50 mM carbonate buffer(pH 9.2) containing 4 M urea. The column was washed with the same buffer containing 20% ethylene glycol; then the same buffer containing 60% ethylene glycol was added to the column to elute the surface antigen.

The eluted fractions containing surface antigen was combined and filtered with an Amicon diafiltration system (Amicon, U.S.A.) having a molecular cut-off value of 100,000, to remove urea and ethylene glycol in the eluate, and the resulting filtrate was concentrated using the same system.

The amount of the HbsAG in the filtrate was about 546 mg, when measured with AUSZYME® kit (yield: 72.4%).

(Step 5) Gel Filtration Chromatography 8 1 of Sepharose CL-4B(Pharmacia, U.S.A.) was filled in a column, and equilibrated with a phosphate buffer(pH 7.2) containing 0.15 M sodium chloride. The concentrate containing the surface antigen, which was obtained in (Step 4), was passed through the column and eluted with the same buffer to obtain fractions containing the surface antigen.

The amount of the HBsAg (comprises both the intact one and fragmented HBsAG due to protease attack) in the combined fractions was about 540 mg, when measured with Auszyme kit(yield: 71.6%) and the purity of the surface antigen was about 98.2%. The content of the preS2 peptide in the total surface antigen was measured to be about 75% by SDS-PAGE. The purified surface antigen solution, thus obtained, was filtered through a 0.2μ filter(Corning, U.S.A.) and the filtrate was stored at 4° C.

COMPARATIVE EXAMPLE 3

The procedure of Example 2, steps 1 to 4 were repeated using 500 g of the starting cell cake and the supernatant solution obtained in step 3 which contained 135.7 mg of the antigen was subjected to column chromatography using a DEAE-sepharose CL6B resin(Pharmacia, Sweden) instead of a phenyl agarose column. The amount of the surface antigen not adsorbed onto the DEAE-sepharose CL6B resin in the initial loading step was 45.49 mg, i.e., about 33.5% of the total antigen present in the solution. This should be contrasted with the case where there was no loss of the antigen during the loading step, i.e., 100% adsorption of the antigen, when the phenyl agarose column of Example 2 was used.

EXAMPLE 3

(Step 1) Disruption of Yeast Cells

Recombinant *Saccharomyces cerevisiae* KCTC 0098BP was cultured at 27° C. in 300 l of YEPD medium. 4 kg of yeast cell cake, thus obtained, was mixed with 8 l of buffer 1 and the mixture was passed twice through Dynomill (Glenmills, Japan) containing 3 e of glass beads having a diameter of 0.5 mm, at 10° C. in a flow rate of 650 ml/min. to disrupt the yeast cells.

The resulting cell homogenate was separated from glass beads, the glass beads were washed with 12 l of buffer 1, and the washed solution was combined with the cell homogenate.

(Step 2) Extraction and Dissolution of the Surface Antigen

To the cell homogenate obtained in (Step 1) was added 0.1%(w/v) of Tween 20 and the mixture was stirred at room temperature for 2 hours.

To the solution was added a saturated ammonium sulfate solution to a final concentration of lot and the mixture was stirred at room temperature for 1 hour. The resulting solution was centrifuged at 8° C. to remove the cell debris together with the precipitates.

The supernatant was filtered with an Amicon diafiltration system(Amicon, U.S.A.) having a molecular cut-off value of 100,000 using 20 mM Tris buffer(pH 7.5), to remove thiocyanate and sodium sulfate therein, and then concentrated using the same system to a final volume of 6 l.

The concentrate was adjusted to pH 11.5 by the addition of 5 N sodium hydroxide and stirred at room temperature for 1 hour. The resulting solution was adjusted to pH 5.2 by adding gradually 20% acetic acid, stirred at room temperature for 30 min. and then allowed to stand for 30 min. The solution was centrifuged at 8° C. to remove the cell debris together with the precipitates.

The supernatant was adjusted to pH 7.2 with the addition of 5 N sodium hydroxide, and the amount of the HBsAg therein was about 1,400 mg, when measured with Auszyme kit.

(Step 3) Adsorption and Desorption Using Silica The supernatant obtained in (Step 2) was adsorbed onto silica(Aerosil 380) in accordance with the following procedure. Dried silica was mixed with water to make a 10% slurry(dry weight/volume of slurry), 2 l thereof was added to the supernatant obtained in (Step 2), and the mixture was stirred at 4° C. overnight.

The resulting solution was centrifuged at 5,500 rpm for 10 min. to remove the supernatant, and the precipitated silica, whereto the surface antigen was adsorbed, was washed twice with phosphate buffer(pH 7.2) containing 0.15 M sodium chloride.

The washed silica was added to 4 l of 50 mM carbonate buffer(pH 9.5) containing 1 M urea and the mixture was stirred at room temperature for 2 hours to desorb the surface antigen from silica. At this point, the buffer showed pH 9.2. The solution was centrifuged at 8,700 rpm to obtain the supernatant containing the surface antigen.

The amount of the HBsAg in the supernatant was about 840 mg, when measured with Auszyme kit.

(Step 4) Hydrophobic Column Chromatography

To the supernatant obtained in (Step 3) containing the surface antigen was added urea to a final concentration of 4 M, and the resulting solution was passed through a phenyl agarose column which was equilibrated with 50 mM carbonate buffer(pH 9.2) containing 4 M urea. The column was washed with the same buffer containing 20% ethylene glycol; then the same buffer containing 60% ethylene glycol was added to the column to elute the surface antigen.

The eluted fractions containing the surface antigen was combined and filtered with an Amicon diafiltration system (Amicon, U.S.A.) having a molecular cut-off value of 100,000, to remove urea and ethylene glycol in the eluate, and the resulting filtrate was concentrated using the same system.

The amount of the HBsAg in the filtrate was about 527 mg, when measured with Auszyme kit.

(Step 5) Gel Filtration Chromatography 8 l of Sepharose CL-4B(Pharmacia, U.S.A.) was filled in a column, and equilibrated with a phosphate buffer(pH 7.2) containing 0.15 M sodium chloride. The concentrate containing the surface antigen, which was obtained in (Step 4), was passed through the column and eluted with the same buffer to obtain the fractions containing surface antigen.

The amount of the hepatitis B viral surface antigen in the combined fractions was about 480 mg, when measured with Auszyme kit and the purity of the surface antigen was about 98.9%. The preS2 peptide content in the total surface antigen was measured to be about 75% by SDS-PAGE. The purified surface antigen solution, thus obtained, was filtered through a $0.2\mu$ filter(Corning, U.S.A.) and the filtrate was stored at 4° C.

EXAMPLE 4

The immunogenicities of the S and preS2 peptides in the surface antigens obtained in Examples 2 and 3(hereinafter, referred to as "surface antigen 2" and "surface antigen 3") were confirmed in accordance with the following experiments using guinea pigs.

1 ml(200 $\mu$g/ml) of surface antigen 2 or 3 was mixed with 18 ml of phosphate buffer(pH 7.2) containing 0.15 M sodium chloride and the mixture was filtered through a $0.2\mu$ syringe filter. The filtrate was mixed with 1 ml of 3% alhydro gel(Superfos Biosector, Denmark). The above procedure was carried out in a sterile state on a clean bench.

Each of eleven guinea pigs weighing about 350 g each was injected subcutaneously with 1 ml of the surface antigen 2 or 3 composition prepared above, twice at an interval of 15 days. After 30 days from the first injection, blood samples were taken from each guinea pig and the sera were separated therefrom. When the sera were analyzed with Ausab® kit (Abbott, U.S.A.), the rates of antibody formation against S peptides of surface antigen 2 or 3 were 100%, GMTs of surface antigen 2 and 3 were 33.38 and 29.77 mIU/ml, respectively.

The rate of antibody formation against the preS2 peptide was determined in accordance with the following procedure. 50$\mu$l (1 mg/ml) of the preS2 peptide having N-terminal 26 amino acids, which were synthesized with a peptide synthesizer(Applied Biosystems, U.S.A.) using an automated solid-phase peptide synthesis, and 20 $\mu$g (10 mg/ml) of poly L-lysine were added to 200 $\mu$l of 50 mM acetate buffer(pH 4.5). To the mixture was added 10 $\mu$l of 1% EDC(1-ethyl-3-(3-dimethyl-aminopropyl)carbodiimide) and the resulting mixture was reacted at 37° C. for 1 hour. The resultant was diluted with 20 ml of 10 mM carbonate buffer(pH 9.6) and added to the wells of 96-well ELISA plate in an amount of 200 $\mu$l/well. The plate was incubated at room temperature for 20 hours to allow the peptide adsorption onto the well surface and then washed three times with distilled water.

PBS containing 0.5% casein was added to the wells in an amount of 250 $\mu$l/well; and the plate was incubated at room temperature for more than 2 hours so as to prevent any non-specific reactions which may occur later. To each of the wells were added positive and negative controls and 200 $\mu$l of each of the guinea pig sera which were serially diluted by ten times with PBS (experimental group). The plate was incubated at room temperature for 4 hours and then washed five times with TTBS buffer(0.9% sodium chloride, 0.05% Tween 20, 10 mM Tris, pH 7.5). A solution comprising porcine anti-guinea pig antibody labelled with horseradish peroxidase(HRP), which was diluted with 4000-fold volume of PBS containing 0.5% casein, was added to the wells in an amount of 200 $\mu$l/well. The resultant was incubated at 37° C. for 1 hour and washed 5 times with TTBS buffer.

Thereafter, 200 $\mu$l of substrate solution for horseradish peroxidase, which was prepared by dissolving 200 $\mu$g of tetramethyl benzidine(TMB) in 20 $\mu$l of DMSO, adding 10 ml of 0.1M acetate buffer(pH 5.1) and 20 $\mu$l of 30% hydrogen peroxide thereto and adjusting the volume of the solution to 20 ml with the addition of distilled water, was added to each well and reacted until the color developed. To the resultant was added 500 $\mu$l of 1N sulfuric acid per each well to stop the color development; and O.D. of each well was determined at the wavelength of 450 nm with Microplate reader(Dynatech MR5000, U.S.A.).

When the O.D. of the experimental group was higher than the cut-off value(twice of the O.D. value of the negative control), it was determined that the antibody formation against the preS2 peptide has occurred and the number of guinea pigs shown positive antibody reaction was counted.

As a result, both of the surface antigens 2 and 3 showed antibody formation rate of 100%.

EXAMPLE 5

In order to determine the immunogenicity of the S and preS2 peptides in the surface antigens 2 and 3, the following experiments using mice was carried out. 1 m$^{-}$(200 $\mu$g/ml) of surface antigen 2 or 3 was mixed with 18 ml of phosphate buffer(pH 7.2) containing 0.15 M sodium chloride and the mixture was filtered through a $0.2\mu$ syringe filter. The filtrate was mixed with 1 ml of 3% alhydro gel(Superfos Biosector, Denmark).

The resulting solution containing 10 $\mu$g/ml of the surface antigen 2 or 3 was diluted with an alhydro gel diluent(which was prepared by diluting alhydro gel) to a final concentration of 0.15% with phosphate buffer(pH 7.2) containing 0.15 M sodium chloride, to make 4 samples having 0.01, 0.03, 0.09 and 0.27 ng/ml of the surface antigen, respectively. The containers containing the samples were shaken sufficiently to prevent precipitation of the alhydro gel. The above procedure was carried out in a sterile state on a clean bench.

Eighty 5-week old mice were divided into 8 groups each consisting of 10 mice and each mouse was injected peritoneally with 1 ml of each of the diluted solutions of surface antigen 2 or 3 prepared above. After 28 days from the injection, blood samples were taken from each mouse and the sera were separated therefrom. The antibodies against S peptide were determined with Ausab kit(Abbott, U.S.A.), and the above antibody formation rates against S peptides in surface antigen 2 or 3 are listed in Table 1.

TABLE 1

| Concentration of surface antigen | Antibody formation rate against the surface antigen (%) | |
| --- | --- | --- |
| (ng/ml) | Surface antigen 2 | Surface antigen 3 |
| 0.01 | 10 | 10 |
| 0.03 | 20 | 40 |
| 0.09 | 80 | 60 |
| 0.27 | 90 | 100 |

The antibodies against the preS2 peptide were determined in accordance with the method of Example 4, and the above antibody formation rates against the preS2 peptides in surface antigen 2 or 3 are listed in Table 2.

TABLE 2

| Concentration of surface antigen | Antibody formation rate against the surface antigen (%) | |
|---|---|---|
| (ng/ml) | Surface antigen 2 | Surface antigen 3 |
| 0.01 | 10 | 10 |
| 0.03 | 20 | 40 |
| 0.09 | 80 | 60 |
| 0.27 | 90 | 100 |

Effective dose 50($ED_{50}$) of S and preS2 peptides were calculated by the probit method(Finney, D. J., Probit Analysis, 1971) using the antibody formation rates obtained above. As a result, $ED_{50}$ of S and preS2 peptides in surface antigen 2 were 0.0580 and 0.0577 ng/ml, respectively, and those of S and preS2 peptides in surface antigen 3 were 0.0455 and 0.0469 ng/ml, respectively. However, since the content of preS2 peptide in surface antigen 2 or 3 is 75%, $ED_{50}$ of the preS2 peptide is considered to be lower than the calculated value obtained above.

As shown in the above Examples, a hepatitis B viral surface antigen having a high preS2 peptide content and the highly immunogenic S and preS2 peptides therein, can be obtained from recombinant yeast last cells in accordance with the present invention.

While the invention has been described with respect to the above specific embodiments, it should be recognized that various modifications and changes may be made to the invention by those skilled in the art which also fall within the scope of the invention as defined by the appended claims.

What is claimed is:

1. A process for purifying hepatitis B viral surface antigen containing a preS2 peptide obtained from the cells of a recombinant organism, which consists essentially of:
   (a) disrupting the cells in a buffer containing a chaotropic salt or a denaturant to thereby obtain a cell homogenate;
   (b) adding a surfactant to the cell homogenate obtained in step (a) and alkalifying the homogenate to a pH of 11.0 to 13.5 to enhance the solubilization of the surface antigen and to thereby obtain an alkalified homogenate;
   (c) acidifying the alkalified homogenate obtained in step (b) to a pH of 4.5 to 6.0 to precipitate cell debris, lipids and contaminant proteins and to thereby obtain an acidified homogenate;
   (d) centrifuging the acidified homogenate obtained in step (c) to thereby obtain a supernatant solution containing the surface antigen;
   (e) treating the solution obtained in step (d) with silica to adsorb the surface antigen onto the silica, removing the contaminant proteins by washing and desorbing the surface antigen from the silica using a buffer to thereby obtain a fraction of purified surface antigen;
   (f) subjecting the fraction of purified surface antigen obtained in step (e) to hydrophobic column chromatography to thereby obtain fractions containing further purified surface antigen; and
   (g) purifying the fractions obtained in step (f) by size exclusive gel filtration chromatography to thereby obtain the surface antigen in a pure form.

2. The process of claim 1, wherein the chaotropic salt is selected from the group consisting of sodium thiocyanate, potassium thiocyanate, ammonium thiocyanate and guanidium chloride; and the denaturant is urea.

3. The process of claim 1, wherein the concentration of the chaotropic salt in the buffer is from 1 to 8 M.

4. The process of claim 1, which further comprises the steps of: adding a salt to the cell extract obtained in step (b); centrifuging the resulting mixture; removing the cell debris and contaminants; and subjecting the supernatant to diafiltration, prior to step (c).

5. The process of claim 1, wherein the surfactant used in step (b) is polysorbate 20, polysorbate 80, polyoxyethylene octylphenylether or sodium deoxycholate.

6. The process of claim 1, wherein the concentration of the surfactant used in step (b) is from 0.1 to 0.5%(w/v) on the basis of the volume of the cell homogenate.

7. The process of claim 1, wherein the silica used in step (e) has a surface area of 100 to 500 $mm^2/g$.

8. The process of claim 1, wherein the surface antigen is desorbed from the silica in step (e) using a buffer which has a pH of 8.8 to 11.0; and contains urea in a concentration of 1 to 8 M and a surfactant in a concentration of 0.1 to 0.3wt. %.

9. The process of claim 8, wherein the surfactant is sodium deoxycholate.

10. The process of claim 1, wherein the hydrophobic column in step (f) is a phenyl agarose column.

11. The process of claim 1, wherein the hydrophobic column chromatography in step (f) is carried out by passing the fraction containing the surface antigen through a column equilibrated with an equilibrium buffer which has a pH of 8.8 to 11.0 and contains urea in a concentration of 1 to 4 M; washing the column with an equilibrium buffer containing 10–40 wt. % ethylene glycol; and eluting the surface antigen with an equilibrium buffer containing 60–80 wt. % ethylene glycol.

12. The process of claim 1, wherein the size exclusive chromatography in step (g) is carried out using a dextran gel or a polyacrylamide gel having a molecular weight cut-off value of at least 1,000,000.

13. The process of claim 1, wherein the size exclusive chromatography in step (g) is carried out by passing the fraction containing the surface antigen through a column equilibrated with a tris(hydroxymethyl)-aminomethane or phosphate buffer which has a pH of 6 to 8 and contains sodium chloride at a concentration of 0.1 to 0.2 M; and eluting the surface antigen with the same buffer.

\* \* \* \* \*